US010932460B2

(12) United States Patent
Sharma et al.

(10) Patent No.: US 10,932,460 B2
(45) Date of Patent: Mar. 2, 2021

(54) CANDLE DISPENSER

(71) Applicant: S.C. Johnson & Son, Inc., Racine, WI (US)

(72) Inventors: Nitin Sharma, Kenosha, WI (US); Brian T. Davis, Burlington, WI (US); Allyce M. Gilligan, Milwaukee, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 83 days.

(21) Appl. No.: 16/195,076

(22) Filed: Nov. 19, 2018

(65) Prior Publication Data

US 2019/0082673 A1 Mar. 21, 2019

Related U.S. Application Data

(63) Continuation of application No. 14/289,761, filed on May 29, 2014, now Pat. No. 10,238,097.

(51) Int. Cl.
| | |
|---|---|
| *A01M 1/20* | (2006.01) |
| *A61L 9/03* | (2006.01) |
| *A01M 29/14* | (2011.01) |
| *A01M 29/12* | (2011.01) |
| *F21V 35/00* | (2006.01) |

(52) U.S. Cl.
CPC .......... *A01M 1/2088* (2013.01); *A01M 29/12* (2013.01); *A01M 29/14* (2013.01); *A61L 9/03* (2013.01)

(58) Field of Classification Search
CPC ............................... A01M 1/2088; A61L 9/03

USPC .......................................................... 422/125
See application file for complete search history.

(56) References Cited

U.S. PATENT DOCUMENTS

| | | | |
|---|---|---|---|
| 4,781,895 A | 11/1988 | Spector | |
| 5,394,506 A * | 2/1995 | Stein | A61L 9/03 219/202 |
| 6,482,365 B1 | 11/2002 | Soller | |
| 6,503,459 B1 * | 1/2003 | Leonard | A01M 1/2088 422/120 |
| 6,534,079 B1 | 3/2003 | Munagavalasa | |
| 6,663,838 B1 | 12/2003 | Soller et al. | |
| 7,138,130 B2 | 11/2006 | Davis et al. | |
| 7,820,188 B2 | 10/2010 | Varanasi et al. | |
| 8,047,837 B2 | 11/2011 | Furner et al. | |
| 2003/0067770 A1 | 4/2003 | Bonnema et al. | |
| 2003/0086815 A1 * | 5/2003 | Wesley | A61L 9/037 422/5 |

(Continued)

FOREIGN PATENT DOCUMENTS

| | | |
|---|---|---|
| FR | 1404904 A | 7/1965 |
| FR | 2294717 A1 | 7/1976 |

OTHER PUBLICATIONS

International Search Report and Written Opinion issued in corresponding International Application No. PCT/US2015/032101, dated Nov. 16, 2015, 19 pages.

*Primary Examiner* — Holly Kipouros
(74) *Attorney, Agent, or Firm* — Quarles & Brady LLP

(57) ABSTRACT

A refill kit for a device to dispense an air treatment chemical includes a substrate supported on a frame. The substrate is in the form of a puck, and includes sand, a binder, and an air treatment chemical. A candle is also provided, which is suitable to heat the substrate.

20 Claims, 12 Drawing Sheets

(56) References Cited

U.S. PATENT DOCUMENTS

| | | | |
|---|---|---|---|
| 2003/0209554 A1* | 11/2003 | DeStefano | A61L 9/03 220/671 |
| 2006/0039945 A1 | 2/2006 | Davis et al. | |
| 2006/0140595 A1* | 6/2006 | Grabowski | A61H 33/063 392/386 |
| 2007/0183981 A1* | 8/2007 | Varanasi | A01M 1/2077 424/40 |
| 2008/0110450 A1 | 5/2008 | Wu | |
| 2009/0004067 A1* | 1/2009 | Furner | A01M 1/2088 422/126 |
| 2009/0004614 A1 | 1/2009 | Furner et al. | |
| 2009/0051263 A1* | 2/2009 | Hayashi | A01M 1/2083 313/485 |
| 2012/0251962 A1 | 10/2012 | White | |
| 2014/0010715 A1 | 1/2014 | Furner et al. | |

\* cited by examiner

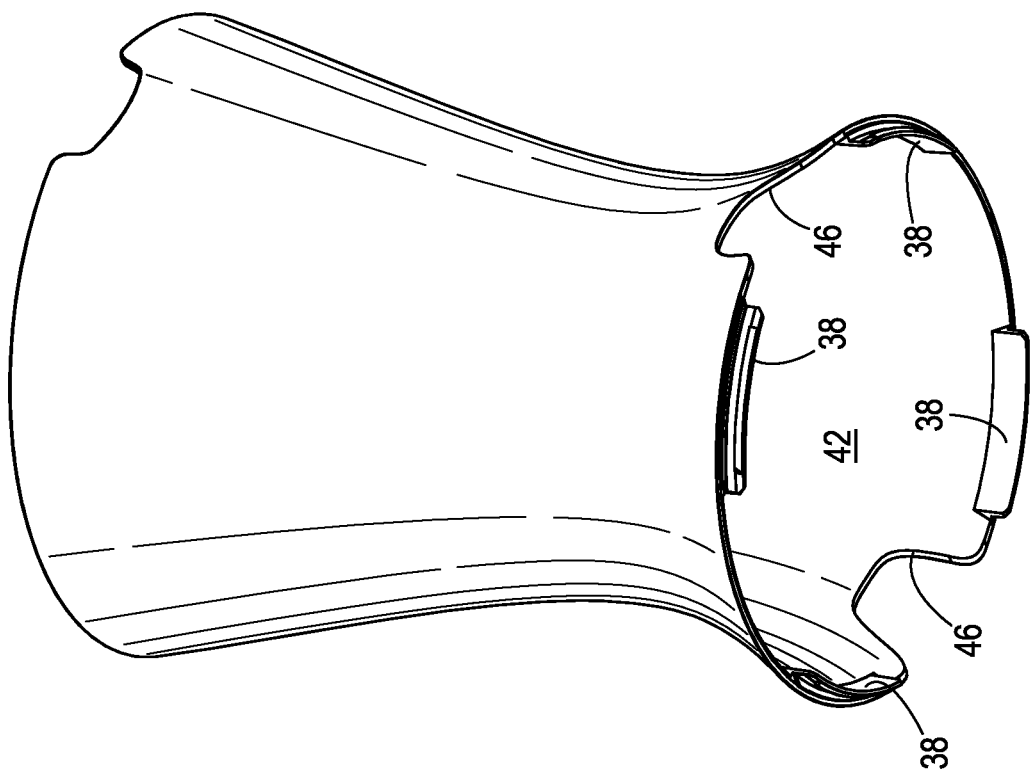
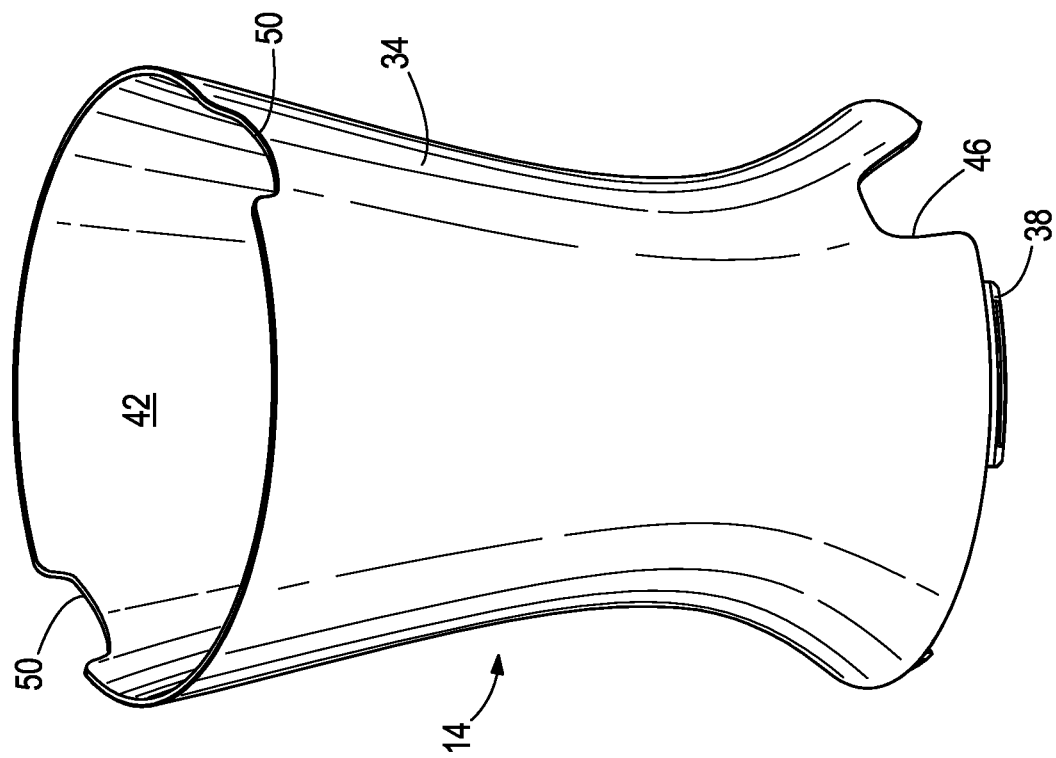

CANDLE DISPENSER

CROSS-REFERENCE TO RELATED APPLICATIONS

This application is a division of U.S. patent application Ser. No. 14/289,761, filed on May 29, 2014, which is hereby incorporated by reference in its entirety.

STATEMENT REGARDING FEDERALLY SPONSORED RESEARCH/DEVELOPMENT

Not applicable

BACKGROUND OF THE INVENTION

The present invention relates to devices that dispense air treatment chemicals ("actives") from a substrate using the heat of a candle to drive the dispensing. More particularly, the invention relates to such devices that dispense the active over a prolonged period in a relatively consistent manner that provides effective coverage throughout an area such as an outdoor patio.

A variety of devices are known for dispensing volatilizable air treatment chemicals such as pest control materials (e.g., insecticides, insect repellants, or insect growth control regulators), air scents or deodorizers (e.g., masks), allergen control ingredients, disinfectants, sanitizers or other materials. In some of these devices the air treatment chemical is mixed with candle wax and is dispensed during candle burning (where the chemical is released primarily from the heated wax surrounding the wick). While this is a common technique for dispensing a variety of fragrances, typically it has been less successful when dispensing certain particularly desirable pest control materials.

Attempts have been made to use heat from a candle to distribute air treatment chemicals from an adjacent impregnated pad surface. See e.g., U.S. Pat. Nos. 4,781,895, 7,138,130 and 8,047,837. However, it is difficult to design such devices to work over a four hour, six hour or even longer period (four to six hours being a typical period for a dinner party or picnic) while consistently distributing enough chemical to be effective in a large area throughout that period.

Some attempts have been made to use electrical heaters to drive air treatment chemicals in a more controlled manner from a substrate or reservoir. See U.S. Pat. No. 7,820,188. However, such systems required structures to generate, store, and/or accommodate electrical power, which increases the cost of the device.

U.S. Patent application publication 2012/0251962 taught a trapeze-like structure for lowering a candle into a glass chimney, but was not directed to dispensing a volatizable air treatment chemical.

Thus, a need exists for low cost air treatment chemical dispensers where heat drives an air treatment chemical off of a carrier substrate in a way which provides prolonged useful life and capability of treating a large area.

BRIEF SUMMARY OF THE INVENTION

In one aspect, a refill kit for a device to dispense an air treatment chemical is provided. The refill kit includes a substrate supported on a frame, the substrate being in the form of a puck. The substrate includes sand, a binder, and an air treatment chemical. A candle is also provided, which is suitable to heat the substrate.

In some embodiments, the frame further comprises a retainer that inhibits removal of the substrate from the frame, an array of vents, or a lift handle. In other embodiments, the air treatment chemical is a pest control active ingredient, and a length of time the candle burns is essentially the same as the length of time the air treatment chemical is released at effective levels when heated by the candle.

In yet another embodiment, the puck has a maximum thickness of no greater than 5 cm.

From the discussion below it will be appreciated that various embodiments of the invention achieve a variety of advantages. As these embodiments are merely illustrative, they are not intended to represent the full scope of the invention. Thus, reference should therefore be made to the claims herein for interpreting the full scope of the invention.

BRIEF DESCRIPTION OF THE DRAWINGS

FIG. 4 is an upper perspective view of the housing of the candle dispenser of FIG. 1;

FIG. 5 is a lower perspective view of the FIG. 4 housing;

DETAILED DESCRIPTION OF THE PREFERRED EMBODIMENTS

Figure 1A:
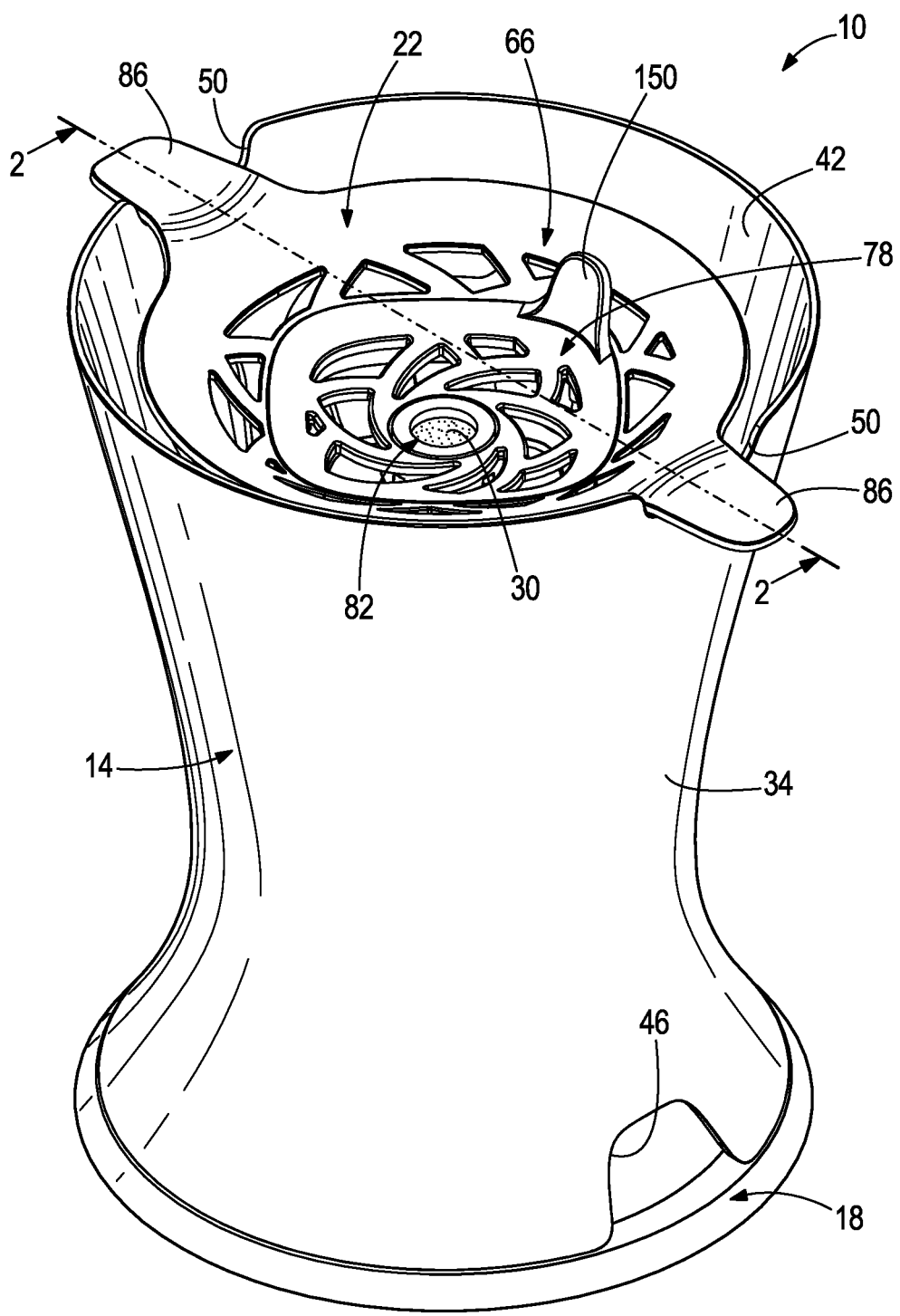
FIG. 1A is an upper perspective view of a candle dispenser of the present invention, where the outer chimney is translucent.
Figure 1B:
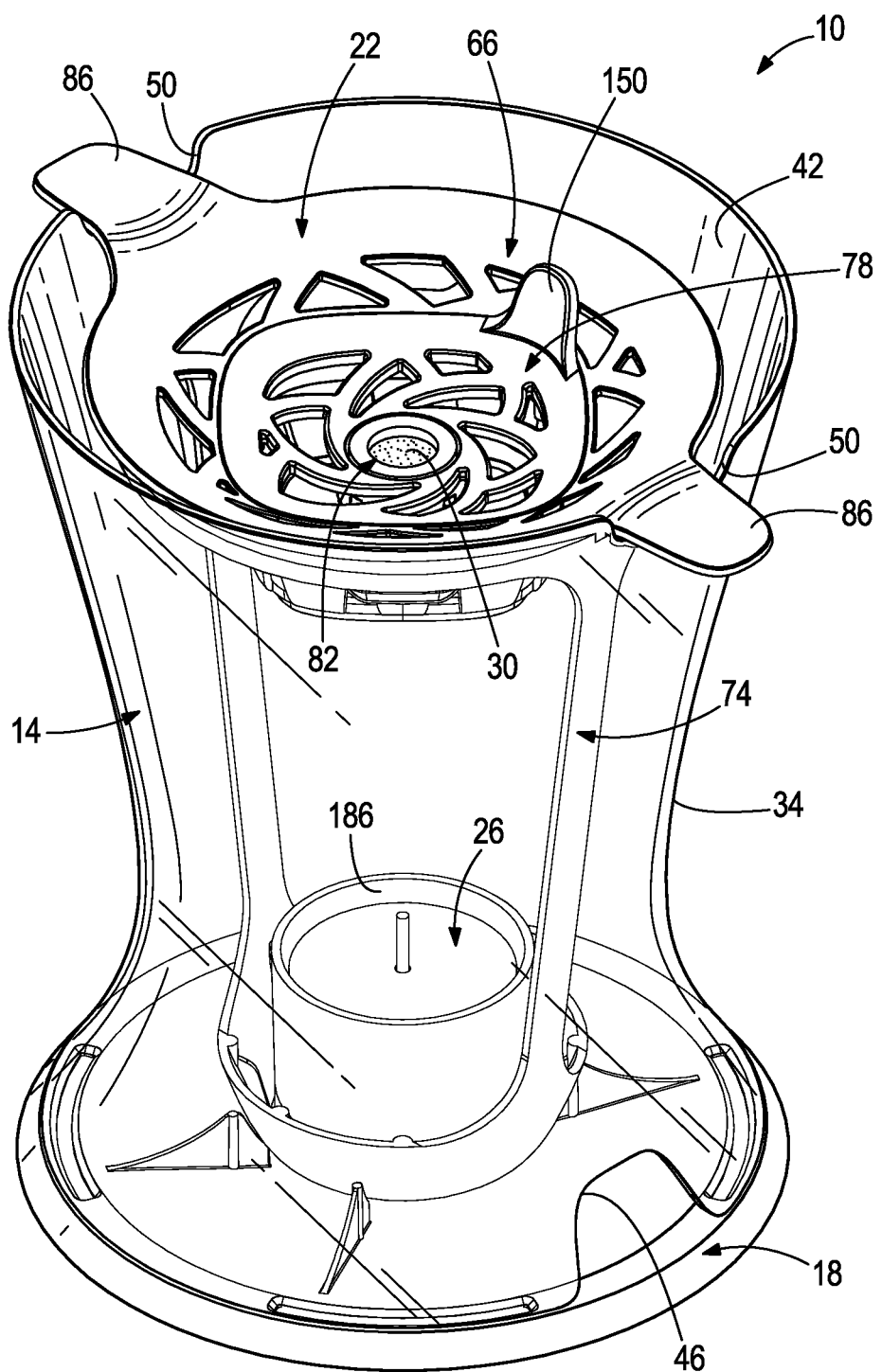
FIG. 1B is a view identical to FIG. 1A, but where the outer chimney is transparent.
Figure 2:
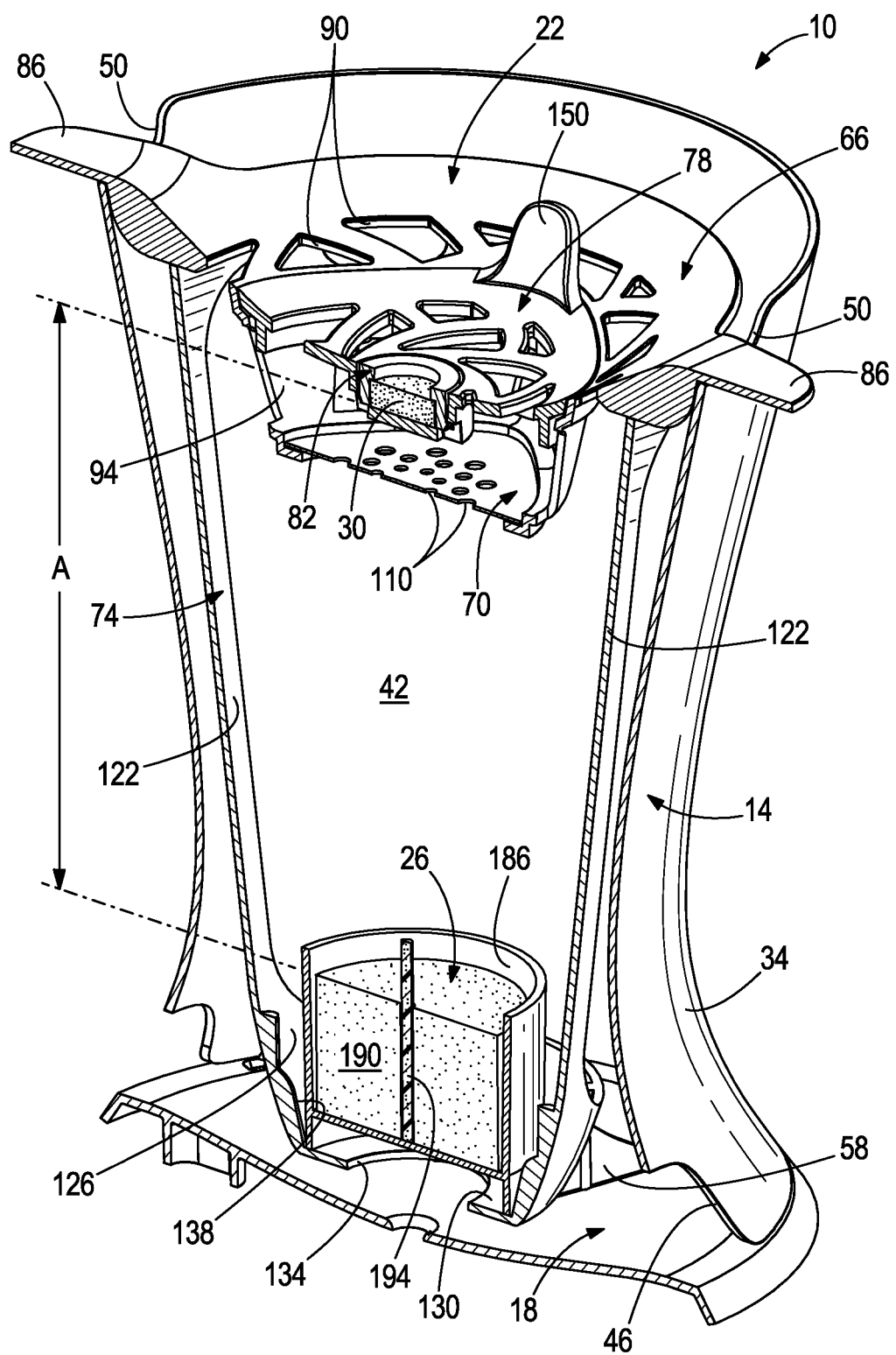
FIG. 2 is a sectional view of the candle dispenser of FIG. 1, taken along line 2-2 of FIG. 1.
Figure 3:
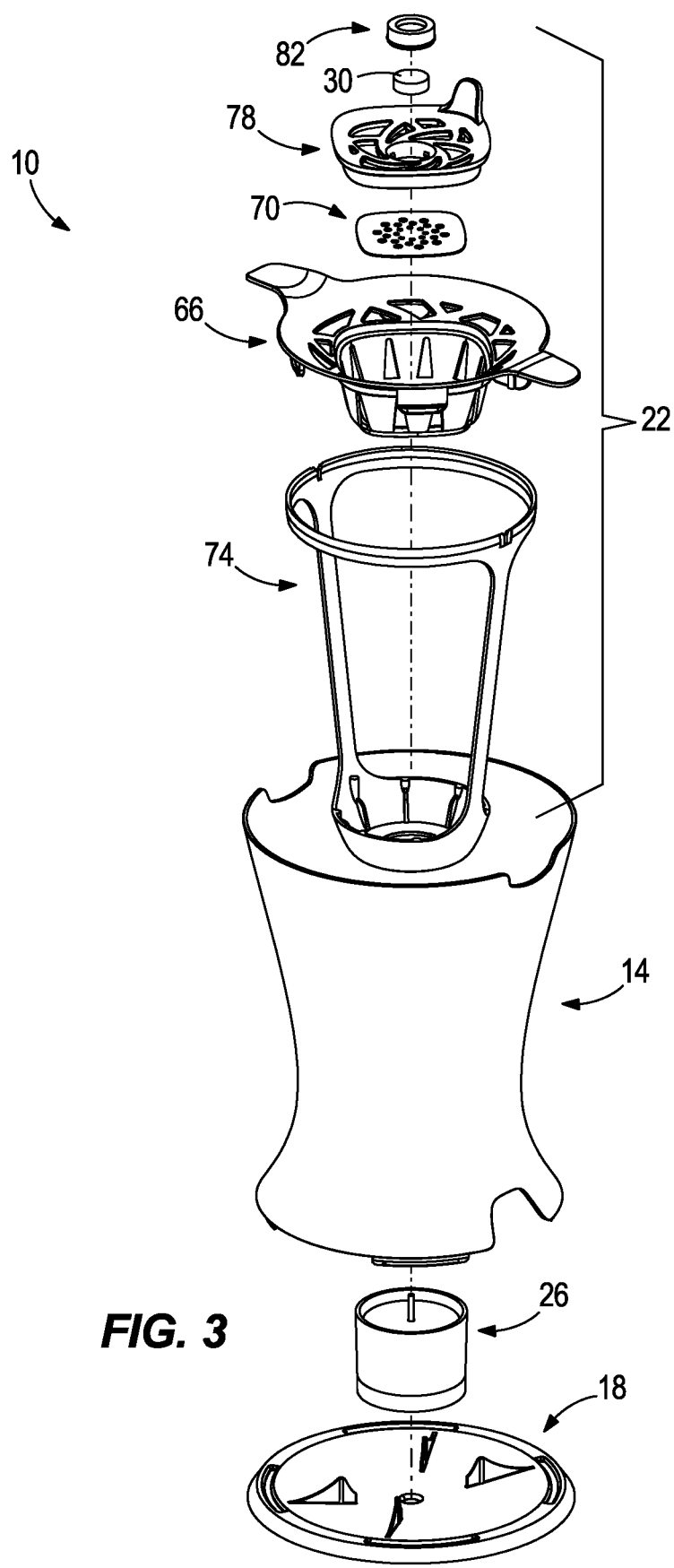
FIG. 3 is an exploded view of the candle dispenser of FIG. 1.

FIGS. 1-3 shows a device in the form of a candle dispenser 10 for dispensing air treatment chemical. The candle dispenser 10 includes a housing 14, a base 18, and an upper caddy 22. With reference to FIG. 2, the upper caddy 22 holds a heat source in the form of a candle 26 and a substrate 30. As shown in FIG. 1B the housing 14 can alternatively be a transparent housing.

As shown in FIGS. 4 and 5, the housing 14 is generally sleeve-shaped and may be referred to as a shade or a chimney. The housing 14 includes a substantially hyperbolic shaped side wall 34 with a curvature and a base engaging structure in the form of four tabs 38. The side wall 34 defines an interior cavity 42 with an open top, an air inlet in the form of two bottom vents 46, and a caddy mounting feature in the form of two caddy recesses 50. The housing 14 may be made of glass or another heat-resistant transparent or translucent material, such as a plastic. A translucent housing 14 would ornamentally hide portions of the upper caddy 22 and structures depending from it, but show light generated from the candle 26.

In other embodiments the base engaging structure may include more or less than four tabs 38, or may be defined by recesses slots, fasteners, or another structure. The air inlet may include more or less than two bottom vents 46 or the air inlet may be spaced a distance from a bottom of the housing 14, as desired. The caddy mounting feature may engage the caddy 22 differently. For example, the caddy mounting feature could include pins, apertures, or another feature, as desired.

Figure 6:
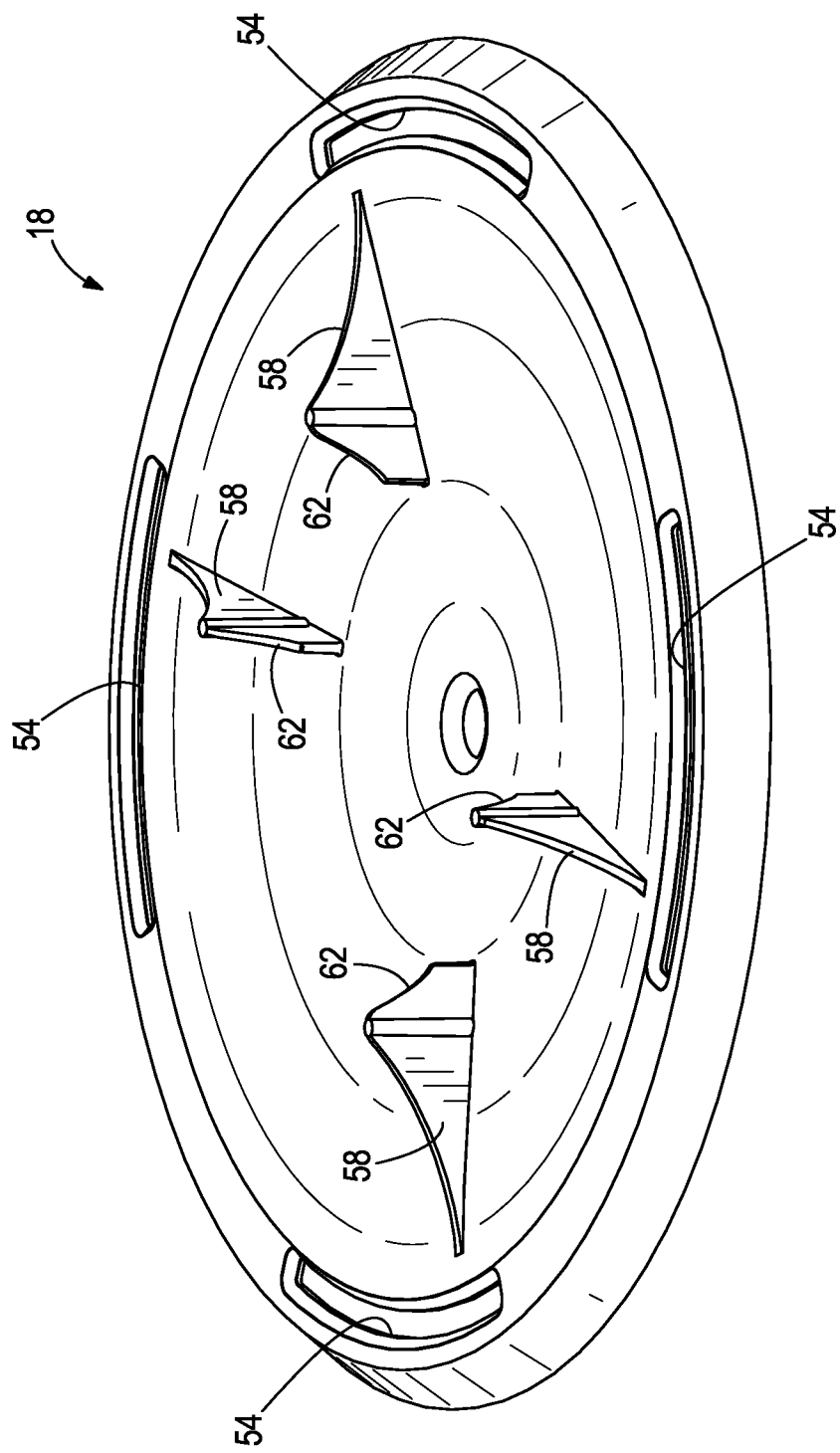
FIG. 6 is an upper perspective view of a base of the candle dispenser of FIG. 1.

As shown in FIG. 6, the base 18 includes a housing engaging structure in the form of recesses 54 sized to receive the tabs 38 of the housing 14. The recesses 54 and tabs 38 are arranged such that the tabs 38 snap into the recesses 54 and maintain the housing 14 attached to the base 18. The base 18 further includes a caddy centering feature in the form of four fins 58. Each fin 58 defines a shaped profile 62 shaped to engage and center the caddy 22 relative to the base 18. The base 18 is also arranged to support the candle dispenser 10 on a surface.

Figure 7:
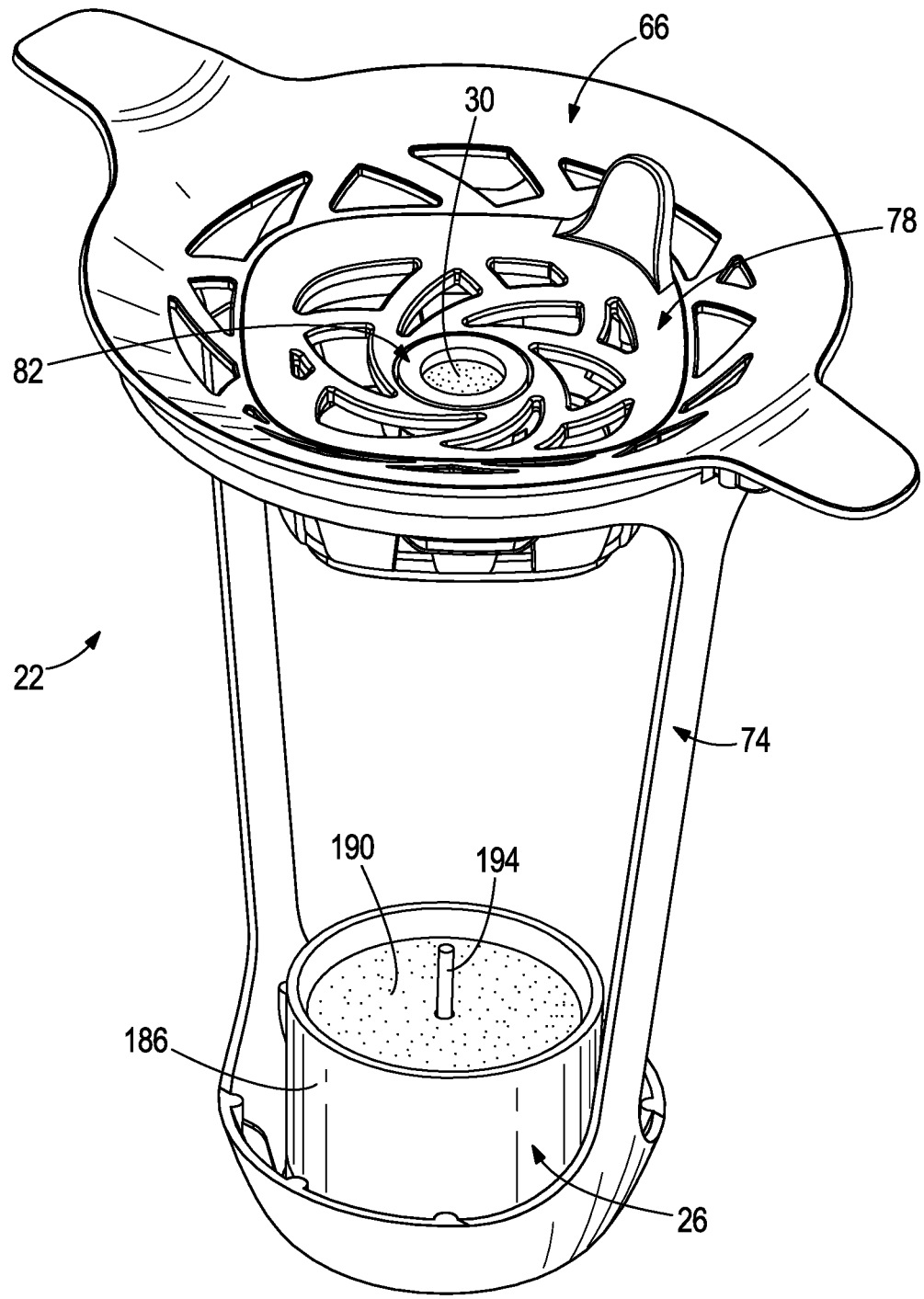
FIG. 7 is an upper perspective view of a caddy assembly of the candle dispenser of FIG. 1, with a candle and refill frame mounted thereon.
Figure 12:
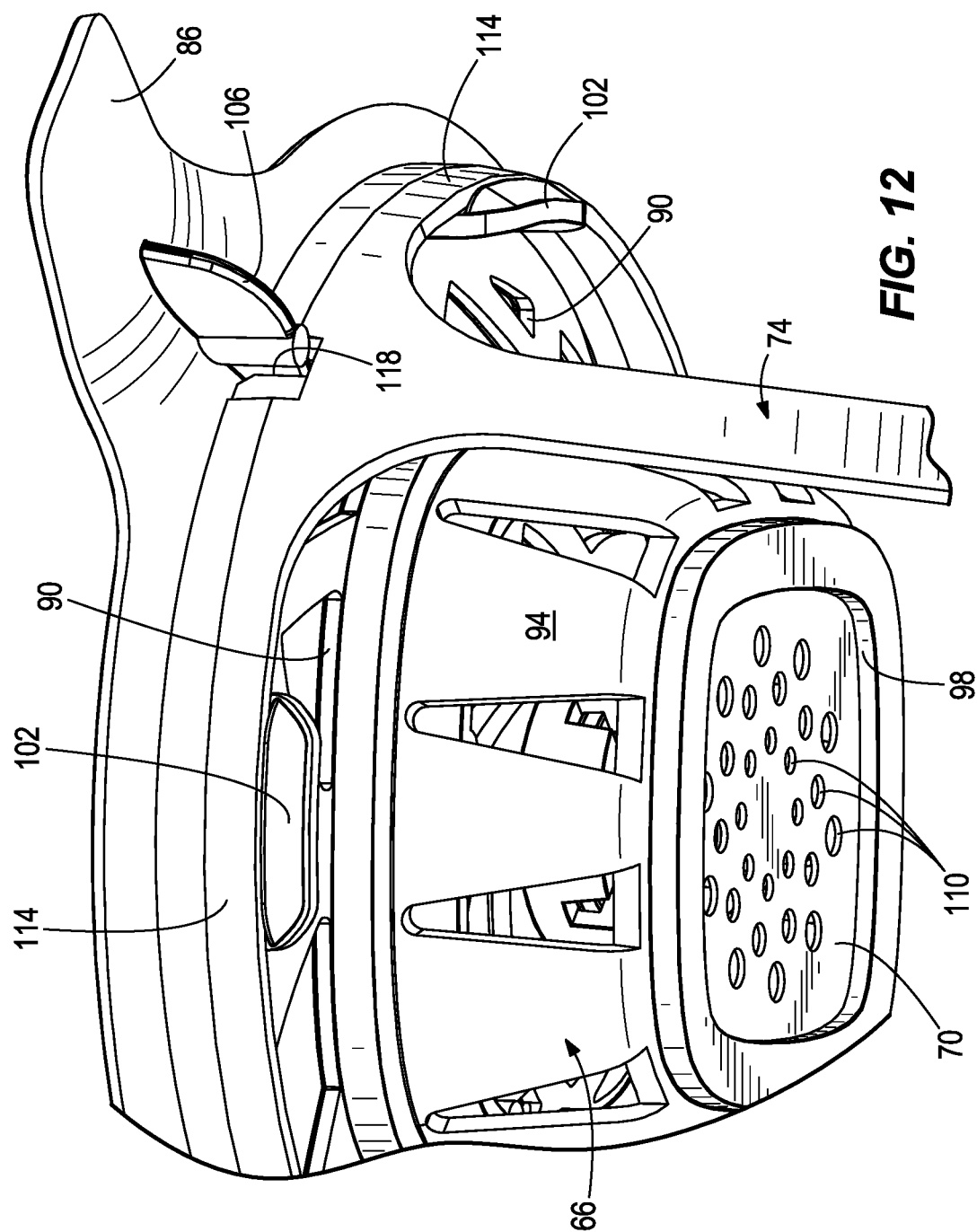
FIG. 12 is an enlarged lower perspective detail view of a portion of the FIG. 7 caddy assembly.

As shown in FIGS. 7 & 12, the caddy 22 includes an upper caddy frame 66, a heat deflector plate 70, lower caddy frame 74 with hanger elements 122, and a candle holder 126, into which the user inserts a candle 26, and a refill frame 78 supporting a substrate 30, preferably including a refill retainer 82.

Figure 8:
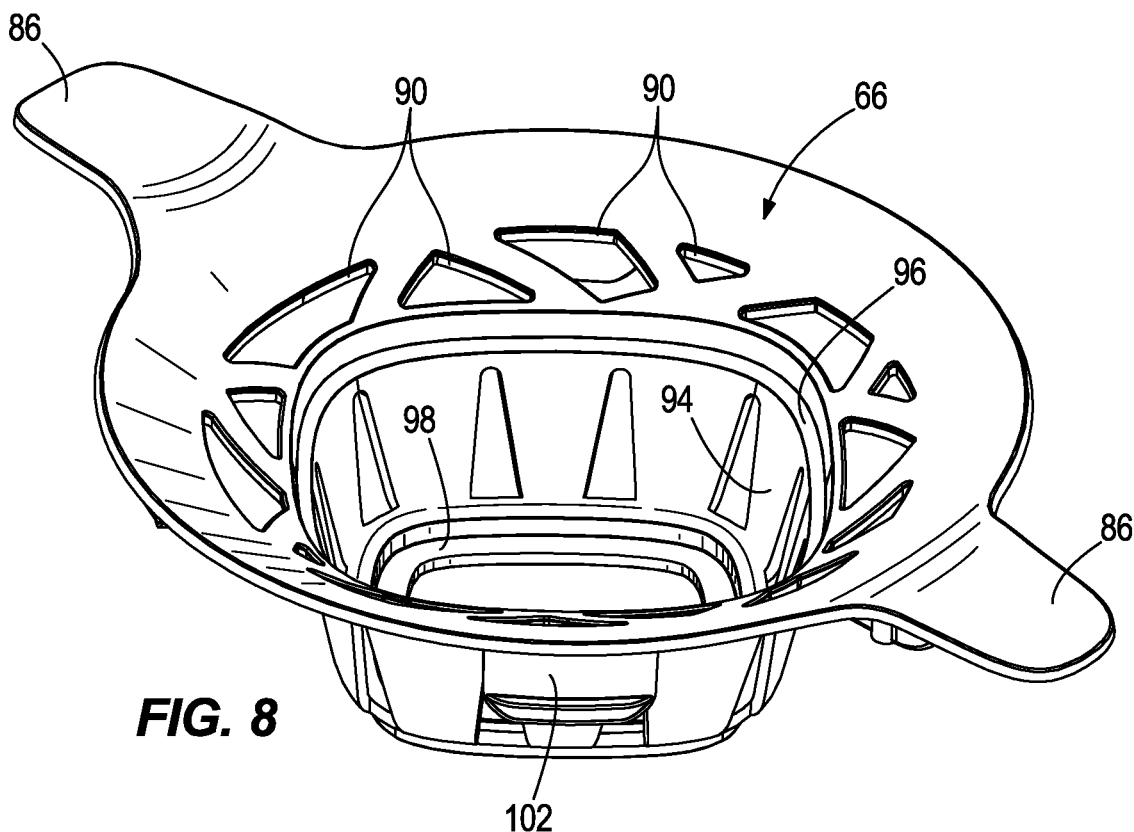
FIG. 8 is an upper perspective view of an upper caddy frame portion of the caddy assembly of FIG. 7.

Turning to FIG. 8, the upper caddy frame 66 includes a housing mounting feature in the form of two lift handles 86 sized to engage the caddy recess 50 of the housing 14. A plurality of vents 90 are formed around a top periphery of the upper caddy frame 66 and are arranged to allow a predetermined airflow therethrough while the candle dispenser 10 is functioning. The upper caddy frame 66 includes a refill receiving feature in the form of a cavity 94 that is sized to receive the refill frame 78 and defines shoulder 96 and a heat deflector engaging structure in the form of a rim 98.

Figure 9:
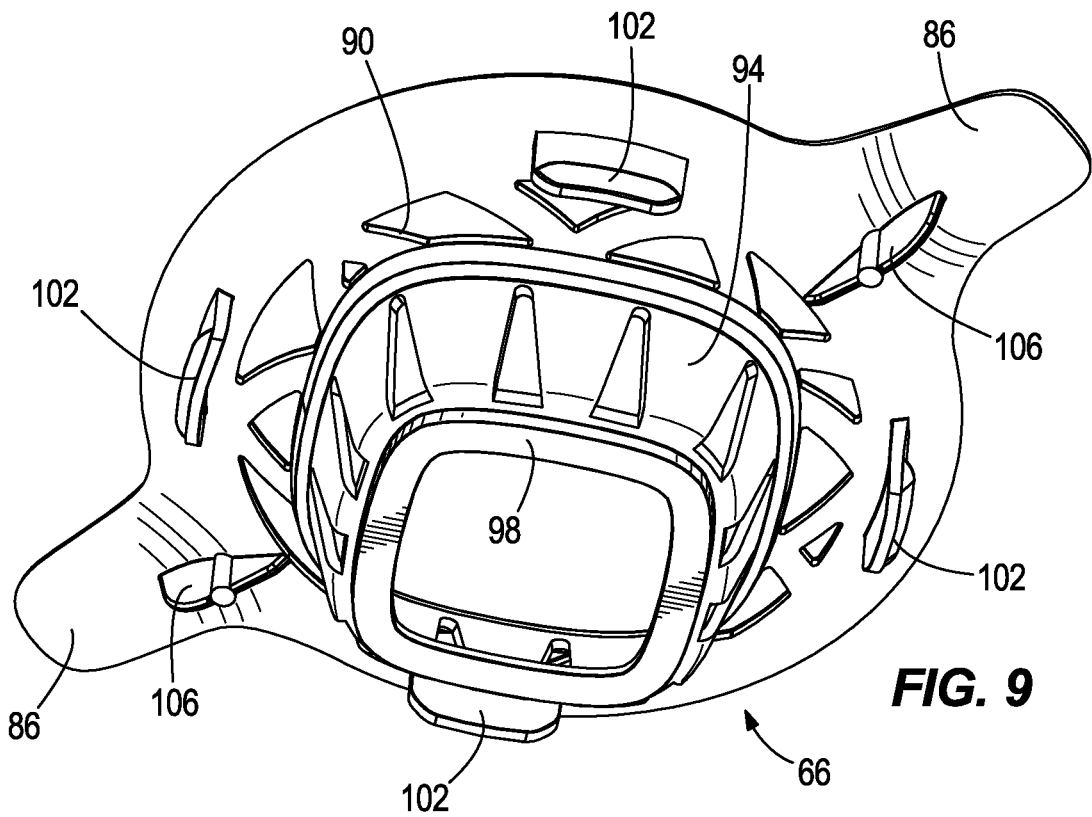
FIG. 9 is a lower perspective view of the upper caddy frame of FIG. 8.

FIG. 9 shows an under side of the upper caddy frame 66 including a lower caddy frame engaging feature in the form of four tabs 102 and two projections or fins 106. In other embodiments, more or less than four tabs 102 and more or less than two fins 106 may be utilized. Additionally, other engaging features may be used (e.g., friction fit, fasteners, adhesive, et cetera) as desired.

Figure 10:
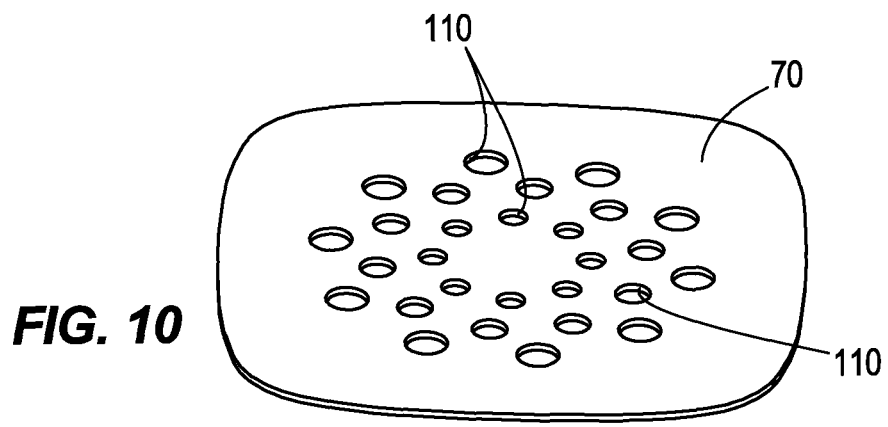
FIG. 10 is an upper perspective view of a heat deflector plate of the caddy assembly of FIG. 7.

The heat deflector plate 70 is shown in FIG. 10 and is sized to be received within the refill receiving cavity 94 of the upper caddy frame 66 and supported on the rim 98. A vent structure in the form of a plurality of holes 110 is formed in the heat deflector plate 70. The illustrated holes 110 are defined by three concentric rings of holes 110. The inner ring defines holes 110 of a first diameter, the middle ring defines holes 110 of a second diameter, and the outer ring defines holes 110 of a third diameter. The holes 110 are sized and arranged to provide a predetermined airflow into the refill receiving cavity 94. Alternatively, the holes may all be of the same size. The heat deflector plate 70 provides a control flow of heat energy toward the substrate 30 and inhibits the overheating or melting of the substrate 30. In other embodiments, the vent structure may be arranged differently. For example, a plurality of slots, or wedge shaped vents may be formed in the heat deflector plate 70, as desired.

Figure 11:
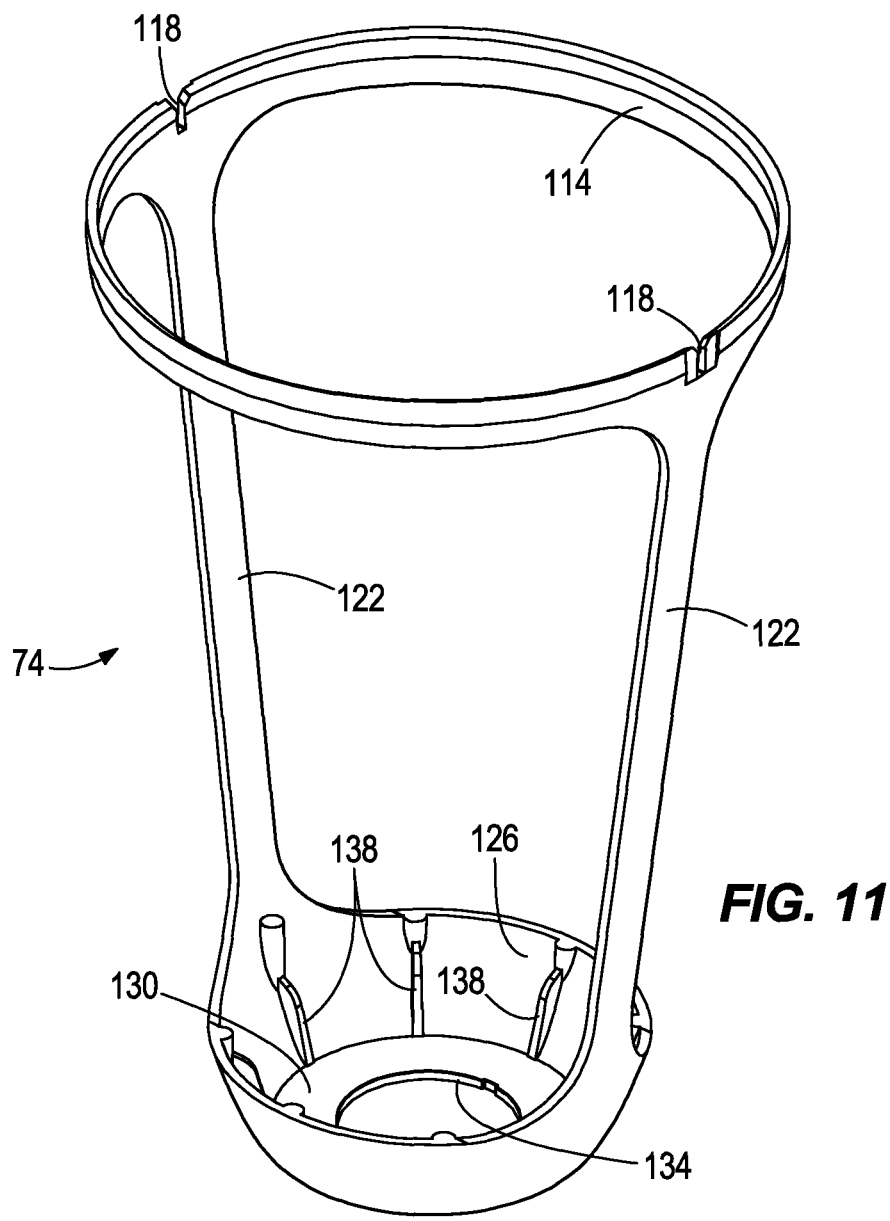
FIG. 11 is an upper perspective view of a candle holder portion of the caddy assembly of FIG. 7 integrally formed with a trapeze hanger structure.

As shown in FIG. 11, the lower caddy frame 74 includes an upper caddy frame mounting feature in the form of a ring 114 sized to be engaged by the tabs 102 of the upper caddy frame 66 and two recesses or slots 118 sized to receive the fins 106 of the upper caddy frame 66.

FIG. 12 shows the tabs 102 engaging the ring 114 (two tabs 102 are visible) and the fins 106 engaging the slots 118 (one fin 106 and slot 118 are visible). When assembled as shown in FIG. 12, the upper caddy frame 66 and the lower caddy frame 74 are substantially rigidly mounted to one another such that there is no substantial movement of one component relative to the other.

The lower caddy frame 74 also includes two extension elements 122 that space a candle holder 126 away from the ring 114. More than two or less than two extension elements 122 may be utilized or the extension elements may have a different shape, so long as they support the candle holder 126 spaced apart from the upper caddy frame 66 when the lower caddy frame 74 and the upper caddy frame 66 are assembled.

The candle holder 126 includes a support surface 130 for supporting the candle 26, a candle aperture 134 formed through the support surface 130, and a centering feature in the form of ribs 138. The support surface 130 provides a solid base that holds the candle 26 when in use. The candle aperture 134 is sized such that a standard tea candle will fall through the candle aperture 134 and not be supported on the support surface 130. The candle 26 is specially designed to operate with the candle dispenser 10 and the candle aperture 134 helps the end user ensure a most appropriate candle 26 is being used such that the candle dispenser 10 can function to its intended potential (e.g. a specified heating range). Specifics of the candle 26 will be discussed below. The ribs 138 maintain the candle 26 in a centered position on the support surface 130.

Figure 13:
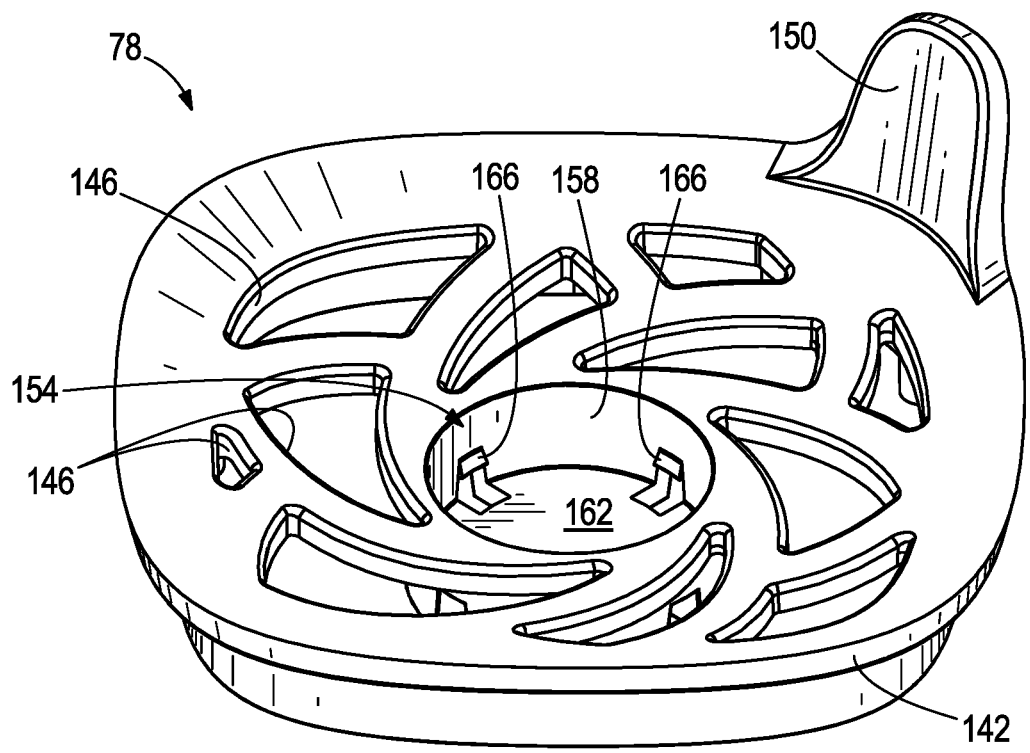
FIG. 13 is an upper perspective view of a refill frame of the caddy assembly of FIG. 7.

As shown in FIG. 13, the refill frame 78 includes a flange 142 sized to be supported on the shoulder 96 of the refill receiving cavity 94, a vent structure in the form of a plurality of apertures 146, a handle 150, and a substrate receiving feature 154. The apertures 146 are sized and arranged to permit a predetermined airflow therethrough. The handle 150 provides an easily graspable feature that allows a user to remove and install the refill frame 78 with ease. In other embodiments, the vent structure may be arranged differently. For example, a plurality of slots, a spiral pattern, or another structure may be utilized to provide the desired airflow. Additionally, the handle 150 may take another form. More than one handle 150 may be formed on the refill frame 78, or positioned on a different area of the refill frame 78, as desired.

The substrate receiving feature 154 includes a sidewall 158, a base or floor 162, and a substrate retaining feature in the form of four tabs 166 (two tabs 166 are visible in FIG. 13). The sidewall 158 is substantially cylindrical, although other shapes are considered to match the desired substrate 30. For example, the sidewall may be square, rectangle, or another shape. In other embodiments, the floor 162 may include apertures or vent features other than the small openings formed near the tabs 166, as desired.

Figure 14:
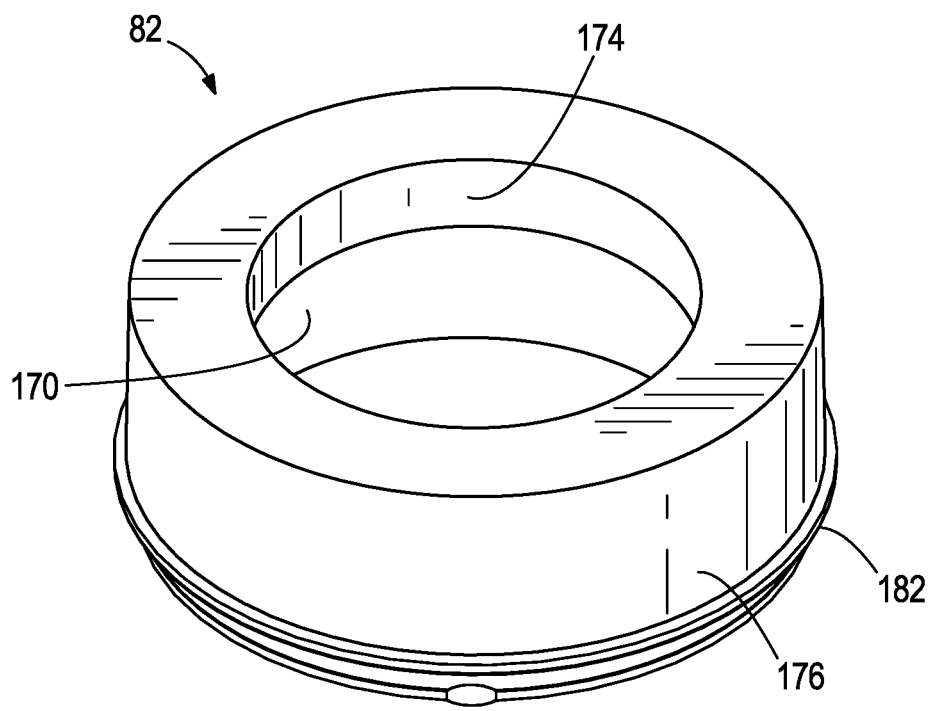
FIG. 14 is an upper perspective view of a refill retainer ring suitable to be used with the FIG. 13 refill frame.

As shown in FIG. 14, the refill retainer 82 includes an interior cavity 170 sized to receive the substrate 30, an upper flange 174 sized to inhibit the substrate 30 from passing therethrough, an outer wall 176 sized to be received within the sidewall 158 of the substrate receiving cavity 154, and a shoulder 182 sized to be engaged by the tabs 166 of the substrate receiving feature 154. The bottom (as shown in FIG. 14) of the refill retainer 82 is open such that the substrate 30 may be received within the interior cavity 170. In other embodiments, the refill retainer 82 may be shaped differently to receive the substrate and mate with the substrate receiving cavity 154. Further, the refill retainer 82 may be eliminated and the substrate 30 maintained in the refill frame 78 by press fit, or another means.

The substrate 30 shown in FIG. 3 is preferably a porous sand core made of sand mixed with novolac (or other resin) binder as well as about 40 milligrams of a pest control active ingredient such as metofluthrin mixed in acetone (e.g., a 30% mixture). In other embodiments the substrate is dosed with between about 25 mg and 150 mg of pest control active ingredient. See generally U.S. Pat. No. 7,820,188 for suitable sand core substrate constructions. The illustrated substrate 30 is generally cylindrically shaped. In other constructions, the substrate may be conically shaped, frusto-conically shaped, square, rounded square, or another shape, as desired.

For purposes of prolonged useful life with effectiveness throughout a relatively large area (e.g. 100 square feet or more), it has been found desirable to configure some of the devices within particular parameters. For example, it has been found desirable for the thickest part of the substrate 30 to be between 0.5 cm and 5 cm thick, preferably about 1 cm thick. In one embodiment, the substrate 30 may be dosed with 25 mg or more of pest control active ingredient (e.g., 70 mg metofluthrin). Metofluthrin tends not to vaporize off of such sand cores absent heating, and has particularly desirable repellency and other characteristics when the substrate 30 is heated to about 120° C. (e.g., 123° C.) at its top surface (about 150° C. at the bottom surface).

One can dissolve the active in acetone or a hydrocarbon before it is dosed on the substrate 30. When the active is applied to the substrate 30 it may be coated on or impregnated in various ways. For example, drops of a mix can be released above the substrate 30 and allowed to disperse through the substrate 30.

Air treatment chemicals to be applied to sand core may include a wide variety of actives. See U.S. Pat. Nos. 6,309,986 and 6,337,080 for disclosure of a variety of insect control materials, deodorizers, fragrances, sanitizers, and disinfectants known to be suitable for use with heating dispensers. For example, suitable active materials may include (when the volatile material is an insecticide and/or insect repellent) organic phosphorous insecticides, lipid-amide insecticides, natural repellents as citronella oil, natural pyrethrins and pyrethrum extract, and synthetic pyrethroids. Suitable synthetic pyrethroids include without limitation acrinathrin, allethrin as D-allethrin, Pynamin, benfluthrin, bifenthrin, bioallethrin as Pynamin Forte, S-bio-allethrin, esbiothrin, esbiol, bisoresmethrin, cycloprothrin, cyhalothrin, lambda-cyhalothrin, cyphenothrin, empenthrin, esfenvalerate, fenpropathrin, fenvalerate, flucythrinate, tau-fluvalinate, kadethrin, metofluthrin, phenothrin, prallethrin as Etoc, resmethrin, tefluthrin, tetramethrin, or transfluthrin. It is preferred to use a highly volatile active when seeking insect control in a large space or outdoors on a patio. It is most preferred to use metofluthrin or transfluthrin when mosquito control is of primary interest in a large outdoor area.

As shown in FIG. 2, the candle 26 includes a cup 186, a wax 190, and a wick 194. The shape of the candle generally reflects the shape of the lower portion of the caddy 22 and is substantially different than the shape of the upward opening of the upper caddy frame 66, such that a user is not confused about where the candle is to be mounted. The cup 186 defines a diameter larger than a standard tea candle such that the candle 26 does not fall through the candle aperture 134 of the lower caddy frame 74 but is supported on the support surface 130. In this way, a user of the candle dispenser 10 is aided in avoiding the use of non-genuine candles (which might provide too little heat to be fully effective). The diameter of the cup 186 also provides that the ribs 138 substantially center the candle 26 with respect to the caddy 22.

The wax 190 is preferably a mix of conventional candle waxes, but presented in a diameter slightly wider than a standard tea candle size. Optionally, another secondary air treatment chemical (e.g., a fragrance, citronella) may be mixed directly in with the wax 190. This wax mix, together with a cotton or other wick 194, generates a very desirable temperature range for the present purposes.

Assembly of the candle dispenser 10 will next be discussed. As shown in FIG. 1, the housing 14 and the base 18 are assembled by engaging the tabs 38 of the housing 14 with the recesses 54 of the base 18 to form a substantially rigid structure. In other embodiments, the housing 14 and the base 18 may be formed as a single structure or may include additional components, as desired.

As shown best in FIGS. 7 and 9, the caddy 22 is assembled by aligning the fins 106 of the upper caddy frame 66 with the slots 118 of the lower caddy frame 74 and engaging the tabs 102 of the upper caddy frame 66 with the ring 114 of the lower caddy frame 74 (see also FIG. 12). The heat deflector plate 70 is then dropped onto the rim 98 of the upper caddy frame 66 (see also FIG. 2). The refill frame 78 is inserted into the refill receiving cavity 94 and supported on the shoulder 96, the substrate 30 is dropped into the substrate receiving feature 154, and the refill retainer 82 is engaged with the substrate receiving feature 154 to lock the substrate 30 in place. The candle 26 is then deposited onto the candle holder 126 by the consumer.

With reference to FIG. 2, the completed caddy 22 is then inserted into the housing 14 such that the lift handles 86 are supported on the caddy recesses 50 of the housing 14.

When the candle dispenser 10 is assembled, the candle 26 is spaced apart from the table or other surface the candle dispenser 10 is resting on such that the candle dispenser 10 may be used even on heat sensitive surfaces. A distance "A" between the candle 26 and the substrate 30 is fixed, as is the distance between the heat deflector plate 70 and the substrate 30. For example, the distance "A" from a top of the candle 26 to a bottom of the substrate 30 may be between 60 mm and 105 mm (e.g., about 95 mm on average).

In addition to the fixed distances, the controlled airflow (e.g., via the various vents and air inlets) maintains the substrate at a remarkably controlled temperature. For example, the substrate 30 may be maintained at approximately 120° C. at a top surface and 150° C. at a bottom surface. At a temperature between 100° C. and 150° C. a substantially consistent level of active release can be achieved for one or more hours. To achieve even better performance beyond six hours (e.g., eight hours over portions of two days) one may trim the wick 194 after use on the first day (e.g., after about four hours).

The various vents/inlets in the candle dispenser 10 are preferably sufficiently small that the candle 26 is unlikely to be accidentally snuffed out by a draft caused by a person walking rapidly by the candle dispenser 10, or by typical wind experienced in patio areas. However, they are large enough to provide sufficient air to the candle 26 to support the flame, disperse heat spikes, and permit dispensing of the active.

When the candle 26 and/or the substrate 30 is used up, the caddy 22 can be lifted out of the housing 14 by the lift handles 86. As will be apparent from FIG. 15, a new candle 26 may be placed in the candle holder 126 and the caddy 22 replaced into the housing 14. To replace the substrate 30, a user may remove the refill frame 78 and replace with a new refill frame 78 including a new substrate 30 and a new refill retainer 82. The subassembly of the refill frame 78, substrate 30, a refill retainer 82, and candle 26 may be purchased as a packaged kit as suggested by the bracketed portion of FIG. 15. Alternatively, only the substrate 30 may be replaced.

Most preferably, the substrate 30 and candle 26 are designed to operate in the candle dispenser 10 with a matching lifespan. That is to say, the candle 26 and substrate 30 are intended to last about the same duration (e.g., 4, 6, or 8 hours) while producing an effective 7-10 mg/hour release rate of the active in the substrate 30. The synchronized duration of the candle 26 and the substrate 30 simplifies the users understanding of when a refill kit is required. In other words, when the user sees the candle 26 is burned out, it is communicated that the candle 26 and the substrate 30 are spent and a new refill kit should be installed.

Figure 15:
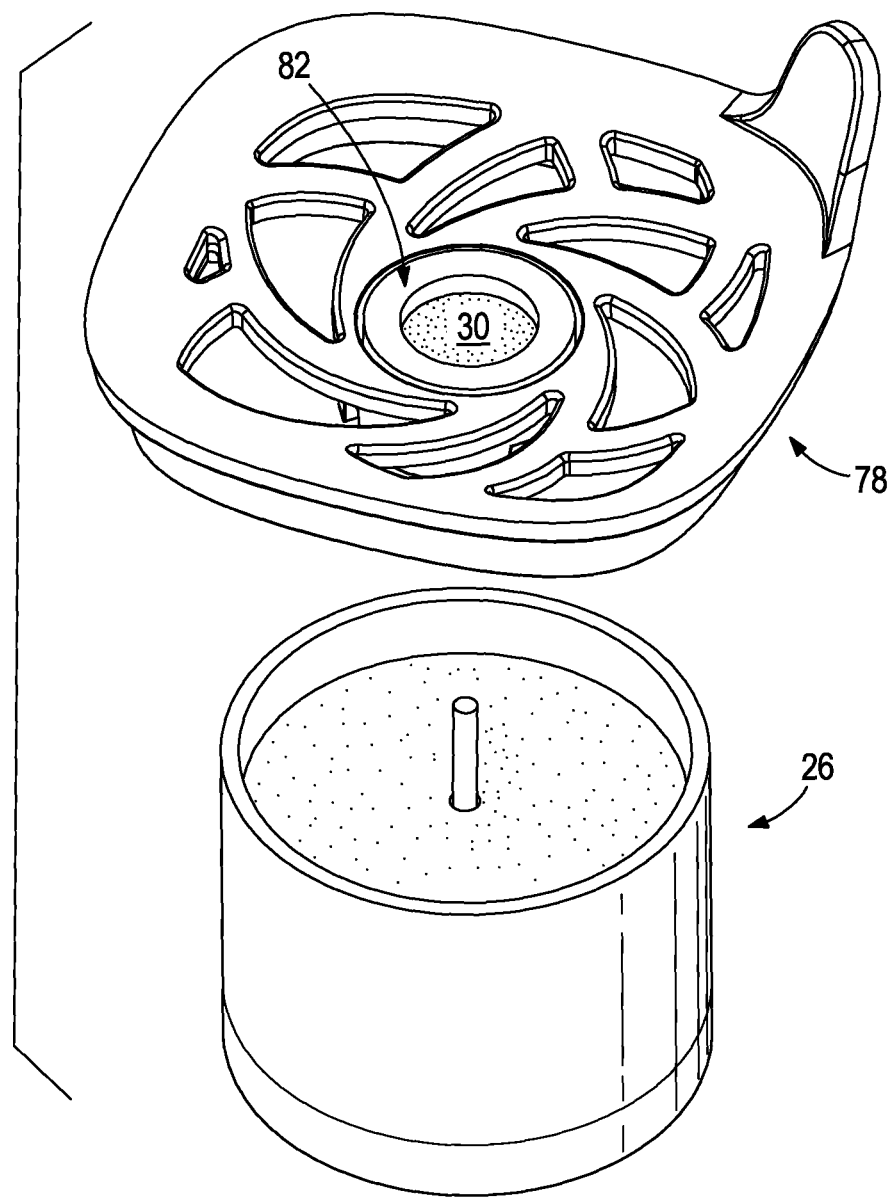
FIG. 15 is an exploded view of the device of the present invention in process of being assembled, with a refill kit portion thereof being highlighted.

As shown in FIG. 15, a substrate 30 supported on the refill frame 78 and a candle 26 can be intuitively used as a refill kit. In a preferred embodiment, proper alignment of the two pieces of the refill kit may be achieved by matching the shape of the refill frame 78 to the shape of the receiving area in the upper caddy, and matching the shape of the candle 26 to the shape of the candle holder.

It will be appreciated that the lower caddy frame 74 helps drop the candle into an appropriate positioning which is further aligned by fins 58 of the base. Also, lift handles 86 then are dropped down into recesses 50 of the outer housing completing the desired alignment.

In sum, the present invention achieves via various embodiments effective and consistent mosquito repellent protection for a relatively large area over a prolonged period. While the above describes preferred embodiments of the present invention, other embodiments are also within the intended scope of the invention. For example, alternative binders can be used in a sand core as described in U.S. Pat. No. 7,820,188 (urethane resins; highly crossed linked thermoplastics). Thus, the invention is not to be limited to just the specific embodiments shown or described herein, and the following claims should be looked to in order to judge the full scope of the invention.

INDUSTRIAL APPLICABILITY

Disclosed herein are improved candle dispenser devices, and refill kits used therewith, particularly those designed to control insects over prolonged periods throughout large areas such as patios.

All documents cited in this patent are, in relevant part, incorporated herein by reference. The citation of any document is not to be construed as an admission that it is prior art with respect to the present invention.

What is claimed is:

1. A refill kit for a device to dispense an air treatment chemical, the refill kit comprising:
a substrate supported on and in contact with a frame; the substrate being in a form of a puck defining a diameter, wherein the substrate is solid throughout the diameter and comprises sand, a binder, and the air treatment chemical; and
a solid wax candle suitable to heat the substrate, wherein the frame further comprises a handle.

2. The refill kit of claim 1, wherein the frame further comprises a retainer that inhibits removal of the substrate from the frame.

3. The refill kit of claim 1, further comprising an array of vents as part of the frame.

4. The refill kit of claim 1, wherein the air treatment chemical is a pest control active ingredient, and a length of time the candle burns is essentially the same as a length of time the air treatment chemical is released at effective levels when heated by the candle.

5. The refill kit of claim 1, wherein the puck has a maximum thickness of no greater than 5 cm.

6. A refill kit for a device to dispense an air treatment chemical, the refill kit comprising:
a cylindrical substrate defining a diameter and supported on and in contact with a frame, the substrate being solid throughout the diameter and comprising sand, a binder, and the air treatment chemical;
a solid wax candle suitable to heat the substrate; and
lift handle positioned on and extending away from the frame,
wherein the frame comprises a receiving feature to secure the substrate to the frame.

7. The refill kit of claim 6, wherein the substrate is secured within a retainer.

8. The refill kit of claim 7, wherein the retainer and the substrate are positioned within the receiving feature.

9. The refill kit of claim 8, wherein the receiving feature has a plurality of retaining features for securing the retainer and the substrate to the frame.

10. The refill kit of claim 9, wherein the retainer includes a shoulder sized to be engaged by the plurality of retaining features.

11. The refill kit of claim 6, wherein a length of time the candle burns is essentially the same as a length of time the air treatment chemical is released at effective levels when heated by the candle.

12. The refill kit of claim 6, wherein the receiving feature comprises a sidewall and a base that match the shape of the substrate.

13. A refill kit for a device to dispense an air treatment chemical, the refill kit comprising:
a cylindrical substrate defining a diameter and supported on and in contact with a frame, the substrate being solid throughout the diameter and comprising sand, a binder, and the air treatment chemical; and
a solid wax candle suitable to heat the substrate from a distance,
wherein the frame comprises a handle and a vent structure in the form of a plurality of apertures.

14. The refill kit of claim 13, wherein the frame includes a flange extending circumferentially around the frame.

15. The refill kit of claim 13, wherein a length of time the candle burns is essentially the same as a length of time the air treatment chemical is released at effective levels when heated by the candle.

16. The refill kit of claim 15, wherein the substrate, the candle, and the frame are replaced after the length of time the candle burns has past.

17. The refill kit of claim 13, wherein the distance is between 60 mm and 105 mm from a top of the candle to a bottom of the substrate.

18. The refill kit of claim 13, wherein the frame further comprises a receiving feature to secure the substrate to the frame.

19. The refill kit of claim 18, wherein the plurality of apertures are located around the receiving feature.

20. The refill kit of claim 13, wherein the air treatment chemical is a pest control active ingredient.

* * * * *